United States Patent [19]

McCurry, Jr. et al.

[11] Patent Number: 5,496,932
[45] Date of Patent: Mar. 5, 1996

[54] PROCESS FOR THE PRODUCTION OF ALKYLPOLYGLYCOSIDE

[75] Inventors: Patrick M. McCurry, Jr., Lansdale, Pa.; Brian A. Michel; Carl E. Pickens, both of Fairfield, Ohio; Janet R. Varvil, Chalfont, Pa.

[73] Assignee: Henkel Corporation, Plymouth Meeting, Pa.

[21] Appl. No.: 47,217

[22] Filed: Apr. 14, 1993

[51] Int. Cl.⁶ .............................. C07H 1/06; C07H 15/02
[52] U.S. Cl. ................... 536/18.5; 536/18.6; 536/124; 536/127
[58] Field of Search ................... 536/18.5, 18.6, 536/127, 124

[56] References Cited

U.S. PATENT DOCUMENTS

| 3,450,690 | 6/1969 | Gibbons et al. | 536/18.5 |
| 4,393,203 | 7/1983 | Mao et al. | 536/124 |
| 4,987,225 | 1/1991 | Pickens et al. | 536/124 |
| 5,079,350 | 1/1992 | Fujita et al. | 536/18.6 |

FOREIGN PATENT DOCUMENTS

| 418458 | 3/1991 | European Pat. Off. . |
| 482325 | 4/1992 | European Pat. Off. . |

*Primary Examiner*—Michael G. Wityshyn
*Assistant Examiner*—Everett White
*Attorney, Agent, or Firm*—Ernest G. Szoke; Wayne C. Jaeschke; Patrick J. Span

[57] ABSTRACT

An improved process for preparing an alkylpolyglycoside wherein the alkyl group contains about 8 to about 20 carbon atoms, prepared by reacting a saccharide and an alcohol in the presence of an acid catalyst, and subsequently removing excess unreacted alcohol, the improvement comprising adding to the reaction product an oxide, such as MgO, and removing the excess unreacted alcohol by thin film evaporation under vacuum at temperatures up to about 240° C. under sparging or non-sparging condition with an inert gas.

18 Claims, No Drawings

5,496,932

PROCESS FOR THE PRODUCTION OF ALKYLPOLYGLYCOSIDE

BACKGROUND OF THE INVENTION

1. Field of the Invention

This invention relates to an improved process of preparing an alkylpolyglycoside by the reaction of a saccharide and a higher alcohol in the presence of an acid catalyst and particularly to the removal of the excess alcohol from the reaction product.

2. Statement of Related Art

Alkylglycosides are conveniently prepared by reacting an alcohol of the type and chain length which is desired to form the "alkyl" portion of the glycoside of interest with a saccharide reactant. Typically such reaction is conducted at an elevated temperature and in the presence of an acid catalyst. Various alkylglycoside products and processes for making same are disclosed in a variety of representative patents. U.S. Pat. No. 4,987,225 contains an extensive listing of processes for preparing alkylglycoside compositions. Included therein is U.S. Pat. No. 4,393,203 to Mao et al. (issued Jul. 12, 1983) which includes the step of removal of the excess alcohol in a thin film evaporator. U.S. Pat. No. 5,079,350 further describes a method for removing unreacted alcohol from the glycoside surfactant product by contacting the alkylglycoside and alcohol mixture with a sparging stream of inert gas under reduced pressure in a thin film evaporator maintained at a temperature in the range of about 140° C. up to 200° C. The process is described as substantially removing all of the unreacted alcohol and the odor from the glycoside product. At temperatures above 200° C., i.e., 210° C., the color (hue) of the alkylglycoside is described as noticeably deteriorated.

BRIEF SUMMARY OF THE INVENTION

It has now been discovered that removing the excess unreacted alcohol in a thin film evaporator in the presence of an oxide such as magnesium oxide enables the removal of the alcohol at temperatures above 200° C. to very low levels and without significant deterioration in color due to the shorter time to which the reaction product of glycoside and alcohol is exposed to the higher temperature. Thus the MgO inhibits the effects of oxidation, providing reduced degradation and lowers the free alcohol level in the final polyglycoside product. The process of the present invention accordingly comprises
(a) reacting a saccharide and an alcohol in the presence of an acid catalyst and
(b) removal of the excess unreacted alcohol by thin film evaporation in the presence of an oxide, preferably magnesium oxide, in an amount effective to inhibit oxidation and deterioration of the alkylpolyglycoside.

The overall process will comprise reacting the saccharide and alcohol in the presence of an acid catalyst after which the acid catalyst must be neutralized, providing alkylpolyglycoside reaction product containing excess unreacted alcohol; adding an oxide, preferably magnesium oxide, either alone or preceded by a stoichiometric deficiency of NaOH to the reaction product and introducing the reaction product now containing the magnesium oxide to a thin film evaporation zone maintained at a temperature of about 140° C. to up to about 240° C., preferably about 210° C.

Thus, the present invention is an improvement in the process of preparing an alkylpolyglycoside with an alcohol and subsequent removal of excess unreacted alcohol, in which the improvement comprises passing a thin film of the reaction product of the saccharide and alcohol in a thin film evaporator maintained at a temperature of about 140° C. up to about 240° C. and a vacuum of about 0.1 to about 20 mm of mercury for a time sufficient to remove unreacted alcohol to a level of less than about 3%, preferably less than 1% and most preferably less than 0.5% to about 0.2% without substantial degradation of the color of the resulting alkylpolyglycoside.

DETAILED DESCRIPTION OF THE INVENTION

In view of the Summary above, it is accordingly an object of the invention to provide an improved process for preparing light colored alkylpolyglycosides of a saccharide reacted with an alcohol in the presence of an acid catalyst at elevated temperatures, after which the acid catalyst is neutralized and the excess alcohol removed, to provide a substantially alcohol free alkylpolyglycoside with little degradation and having good color. The substantially alcohol free product is obtained by removal of the alcohol by thin film evaporation preferably in the presence of magnesium in the form of the oxide, MgO.

As described in the related art section above, the initial reaction product of the alcohol and saccharide in the presence of an acid catalyst results in a glycoside product. The product is a mixture of a monoglycoside of the alcohol and various higher degrees of polymerization (DP) polyglycosides in progressively decreasing mole percentage amounts, i.e., the diglycoside (DP2), the triglycoside (DP3) and the higher polyglycosides (DP4 and higher). The typical, statistical distribution of the various oligomers provided referred to as a Flory distribution. While the specific distribution of the various fractions may vary somewhat for various reaction products, the overall distribution curve is the same, though the average DP of the reaction mixture may vary due to the differing distribution of the various fractions, i.e., DP1, DP2, DP3 and higher fractions. Typically, the Flory distribution of the reaction product after removal of the excess alcohol will have an average degree of polymerization above 1.2, i.e., about 1.4, with a monoglycoside content in the range of about 50–70% by weight of the glycoside product. Commercially available products typically have an average Flory DP of about 1.3–1.7.

The glycoside products of the reaction of an alcohol and saccharide may be represented by the formula I:

$$ROG_x \quad (I)$$

wherein R is a residue of an alcohol, O is oxygen, G is a glycoside residue, and x is the average degree of polymerization (DP) resulting from weighting of the various mono-, di-, tri- and higher glycoside fractions present in the product and is a number of from about one to about three. The average degree of polymerization is thus defined as the ratio of saccharide rings to the R groups in the alkyl glycoside. The monoglycoside fraction would have one saccharide ring, the diglycoside would have 2, the triglycoside would have 3 with the higher glycosides having correspondingly more rings, the average of which in the currently available commercial product therefore being typically greater than about 1, generally in the order of about 1.2 to about 1.7, with preferred mixtures at about 1.3 to about 1.7.

The alkyl polyglycoside products represented by the formula above contain a lipophilic group, the R group, and a hydrophilic group, the $OG_x$ group. For detergent or surfactant-use application, the product should have a hydrophilic-lipophilic balance (HLB) of from about 10 to about 16, and preferably about 11 to about 14. The HLB value of a product may be calculated by the formula $$HLB = \frac{([MW_{AGU}] \times DP + MW_O)}{(([MW_{AGU}] \times DP + MW_O) + MW_R)} \times 100/5$$

where AGU is typically the anhydro glucose unit in G having a molecular weight of 162, $MW_O$ is the molecular weight of oxygen and $MW_R$ is the molecular weight of the R group, and DP is the average degree of polymerization as predicted by Flory's statistical treatment.

The lipophilic R groups in the alkyl polyglycosides are derived from alcohols, preferably monohydric, for the detergent, surfactant-use applications and should contain from about 8 to about 20, preferably about 9 to about 18 carbon atoms, with an average of about 10 to about 13 being most preferred, to provide R groups of sufficient length for detergent, surfactant-use applications. While the preferred R groups are saturated aliphatic or alkyl, there may be present some unsaturated aliphatic hydrocarbon groups. Thus, the preferred groups are derived from the fatty alcohols derived from the naturally occurring fats and oils, such as octyl, decyl, dodecyl, tetradecyl, hexadecyl, octadecyl, oleyl and linoleyl, but R groups may be derived from synthetically produced Ziegler alcohols or oxo alcohols containing 9, 10, 11, 12, 13, 14 or 15 carbon atoms. The alcohols of naturally occurring fatty acids typically contain an even number of carbon atoms and mixtures of alcohols are commercially available such as mixtures of $C_8$ and $C_{10}$, $C_{12}$ and $C_{14}$, and the like. Synthetically produced alcohols, for example those produced by an oxo process contain both an odd and even number of carbon atoms such as the $C_9$, $C_{10}$, $C_{11}$ mixtures, which are also available commercially. Glycoside products suitable for treatment in accordance with the present invention also include derivatives of products of the formula I above including, for example, those in which one or more of the normally free (i.e., unreacted) hydroxyl groups of the saccharide moiety, G, have been alkoxylated, preferably, ethoxylated or propoxylated, so as to attach one or more pendant alkoxy or polyalkoxy groups in place thereof. The formula (I) above, in order to encompass both alkoxylated and non-ethoxylated products, may be modified to the formula II:

$RO (R^1O)_y G_x$ (II)

where R, O, G and x are as defined earlier, $R^1$ is a divalent hydrocarbon radical of the alkoxylating agent, typically containing from 2 to about 4 carbon atoms and y is a number having an average value of from 0 to about 12, more preferably 0 to about 5. When y is 0, the formula reduces to formula I above and the product is non-alkoxylated.

Saccharide reactants which can be employed to prepare the aforementioned glycoside surfactants include reducing monosaccharide materials containing 5 or 6 carbon atoms such as, for example, glucose, galactose, mannose, xylose, arabinose, fructose, etc. as well as materials which are hydrolyzable to form monosaccharides such as lower alkyl glycosides (e.g. methyl glycoside, ethyl glycoside, propyl glycoside, butyl glycoside, etc.), oligosaccharides (e.g. sucrose, maltose, maltotriose, lactose, zylobiose, melibiose, cellobiose, raffinose, stachyose, etc.) and other polysaccharides. Such saccharide reactants may be employed in dry (e.g. anhydrous) form or, if desired, may be employed in the form of hydrated solids or aqueous solutions thereof. If utilized in the form of a solution, it is preferred that the resulting reaction mixture contain only small amounts of water, i.e., less than about 1% by weight, preferably less than about 0.5% i.e. less than 0.25 or 0.1%.

While the condition of the preparation of the initial alkyl glycosides reaction mixture employed in the present invention forms no direct part of the alcohol removal step of the present invention, a brief description generally of the preparation follows. The molar ratio of alcohol to monosaccharide in the reaction mixture can vary widely but is typically between about 1.5:1 to about 10:1, and preferably between about 2.0:1 to about 6.0:1. The particular molar ratio chosen depends upon the desired average degree of polymerization (DP) of the monosaccharide reacted with the alcohol. Preferably, the ratio of alcohol to monosaccharide will be chosen to allow the production of an alkyl glycoside product having a DP between about 1.2 to about 1.7, and more preferably about 1.3 and about 1.6.

The reaction between the hydrophobic alcohol reactant and the saccharide reactant to form the glycoside surfactant is typically conducted at an elevated temperature and in the presence of an acid catalyst. As a general rule, said reaction is preferably conducted at a temperature of from about 80° to about 140° C., preferably about 90° to about 120° C., and at pressures (about 10 to about 100 mm Hg absolute), which facilitate water removal, while at the same time maintaining the desired reaction temperatures.

Acid catalysts suitable for use include strong mineral acids such as sulfuric acid and strong organic acids such as para toluenesulfonic acid, methanesulfonic acid, triflouromethanesulfonic acid, mono- or polyalkylated aryl mono- or polysulfonic acids such as dodecylbenzenesulfonic acid, sulfonated carboxylic acids and esters, etc., and macroreticular acidic ion exchange resins such as macroreticular sulfonic acid ion exchange resins, perfluorinatedsulfonic acid resins, etc. Typically, said acid catalyst will be employed in an amount ranging from about 0.0005 to about 0.03 (preferably from about 0.002 to about 0.015) moles thereof per mole of saccharide used.

Typically, the above-described reaction process will be conducted over a reaction period of from about 1 to about 20 (preferably from about 2 to about 10) hours. Upon completion of the reaction, the acid catalyst is typically partially neutralized by an alkaline substance, preferably an alkali metal hydroxide such as sodium hydroxide, used in an amount of none or preferably up to just less than a stoichiometric amount of material needed to neutralize the catalyst. Preferably the mixture is neutralized and adjusted to a pH of about 3 to about 4 prior to addition of magnesium oxide.

The oxide, preferably magnesium oxide, is added to the mixture of glycoside and alcohol prior to removal of the alcohol. While MgO is preferred, other oxides may be employed, such as, aluminum oxide, calcium oxide, or zinc oxide.

The oxide may be added, before or along with the hydroxide employed to partially neutralize the acid catalyst and adjust the pH prior to alcohol removal, or may be added separately just prior to removal of the alcohol. In a continuous process it would be added to the glycoside-alcohol stream as it exits the reactor, or a pre-evaporator, and is carried to the thin film evaporator.

The magnesium oxide is employed in an amount effective to provide from about 150 ppm to about 1500 ppm or less of magnesium in the product after evaporation and removal of the alcohol. The aqueous solution of the substantially alcohol-free alkylpolyglycoside will accordingly, preferably contain less than about 1000 ppm, and more preferably about 500 to about 700 ppm for solutions containing about 50% to about 70% alkylpolyglycoside in water.

The alkylglycoside alcohol reaction product stream, either directly, or after partial evaporation of the fatty alcohol in a pre-evaporator (e.g., a falling film or forced circulation evaporator) now containing the oxide is introduced into a thin film evaporator to provide a liquid film. The thin film may be contacted with a sparging amount of an inert gas such as nitrogen, in which the inert gas is blown into the thin film evaporator to counter-currently contact the moving liquid. It has been found however that the inert gas may be employed in non-sparging amounts under which temperatures above 200° C. up to about 240° C. may be employed. Under these conditions the presence of the MgO, effectively inhibits color degradation so that even under the higher temperature above 200° C., color remains good and minimal or no odor is observed. Accordingly, in the present invention the unreacted excess alcohol may be removed by thin film evaporation of a stream of glycoside and alcohol reaction product containing MgO, and countercurrent contact with an inert gas under sparging or non-sparging conditions at temperatures from about 140° C. to about 240° C. The pressures employed in thin film evaporation will be on the order of 20 mm Hg or less and preferably at a pressure of 1 to about 10 mm Hg or less.

The inert gas employed is preferably nitrogen, argon, or carbon dioxide, however blown steam or mixtures thereof may be employed without adverse effect, at the magnesium levels described earlier.

In thin film evaporation the film thickness is preferably about 10 mm or less, the thickness of the film being largely dependent on the specific evaporator being employed, the temperature and pressure conditions and the viscosity of the reaction product being evaporated. The evaporation will be conducted for a time sufficient to drop the alcohol level to less than about 3% by weight, and preferably below about 1%, down to 0.5% or less. With the presence of magnesium oxide, permitting higher temperature levels, alcohol levels of about 0.5% down to about 0.2% or less can be accomplished in the present invention. The inert gas may be introduced at the bottom of the evaporator to flow counter-current to the flow of the liquid film. For an evaporator of about 5,000 to 15,000 pounds/hour feed rate, nitrogen may be introduced in a sparging effective amount of about 12 standard cubic feet per minute (scfm), about 0.4–1.0 weight % preferably 0.56 weight %. However, non-sparging conditions from none to about 0.35 weight %, preferably about 0.14 weight % (about 3 scfm), may be employed with the use of MgO.

EXAMPLE

A pre-evaporated $C_{12-16}$ alkyl polyglycoside product (60–65% dry solids), of glucose and a $C_{12-16}$ alcohol (Lorol 1214A, a mixture of $C_{12}$, $C_{14}$, and $C_{16}$ alcohols originally present in a weight ratio respectively of 68, 26, 6 is introduced at the top of a commercial wiped film evaporator with an external condenser at 2 mm Hg pressure, and a temperature of 220° C. in the wiped zone at a feed rate of 10,000 pounds/hr. Nitrogen is introduced at the bottom of the reactor at a rate of 3 standard cubic feet/minute (scfm) sufficient to prevent deterioration of the internal seal of the rotor bearing in the evaporator, but with no sparging effect. In other runs where sparging is desired a feed rate of the nitrogen of 12 scfm is employed. The film thickness is maintained at about 5 mm or less.

Upon removal of the alcohol to a level of about 0.2 to 0.3% a light colored, alkylpolyglycoside, substantially free of alcohol is removed from the evaporator having little odor.

What is claimed is:

1. A process of preparing an alkylpolyglycoside comprising the steps of
   (a) reacting a saccharide and an alcohol in the presence of an acid catalyst to provide an alkylpolyglycoside stream containing unreacted alcohol;
   (b) adding to said alkylpolyglycoside stream containing the unreacted alcohol an oxide selected from the group consisting of aluminum oxide, magnesium oxide, calcium oxide and zinc oxide;
   (c) contacting a liquid film of the oxide containing alkylpolyglycoside and alcohol stream with an inert gas at temperatures of from about 140° C. to about 240° C. and a pressure less than about 20 mm Hg to remove the unreacted alcohol and
   (d) recovering a low odor, light color alkylpolyglycoside containing less than about 5% by weight alcohol.

2. A process as defined in claim 1 wherein the acid catalyst in the alkylpolyglycoside stream is partially neutralized and the pH adjusted to about 3 to about 4.

3. A process as defined in claim 1 wherein the oxide added to the alkylpolyglycoside stream containing unreacted alcohol is MgO.

4. A process as defined in claim 3 wherein the MgO is present in an amount effective to provide from about 150 ppm to about 1500 ppm or less of magnesium after evaporation of the unreacted alcohol.

5. A process as defined in claim 1, wherein said inert gas is nitrogen and is employed in a sparging effective amount.

6. A process as defined in claim 5, wherein said inert gas is nitrogen and is employed in a non-sparging amount.

7. A process as defined in claim 5 wherein said inert gas is nitrogen and the temperature is about 200° C.

8. A process as defined in claim 1 wherein the temperature in step (c) is above 200° C.

9. A process as defined in claim 8 wherein the liquid film has a thickness less than about 10 mm.

10. A process as defined in claim 8 wherein the liquid film has a thickness of 4 mm or less.

11. In a process of preparing an alkylpolyglycoside comprising reacting a saccharide with an alcohol in the presence of an acid catalyst in which the alkyl group contains from about 8 to about 22 carbon atoms, neutralizing the acid catalyst and removing the unreacted excess alcohol, the improvement comprising
   (a) partially neutralizing the acid with an amount of a hydroxide just less than the stoichiometric amount necessary to neutralize the catalyst;
   (b) adding to the reaction product of said saccharide and said alcohol an oxide selected from the group consisting of aluminum oxide, magnesium oxide, zinc oxide and calcium oxide; and
   (c) heating the reaction product, now containing the oxide, under vacuum in a thin film evaporator, wherein the thin film has a thickness less than about 10 mm, the temperature is about 140° C. to about 240° C. and the vacuum is from about 0.1 to about 20 mm of mercury.

12. A process as defined in claim 11 wherein the oxide is magnesium oxide in an amount effective to provide from about 150 ppm to about 1500 ppm of magnesium after removal of the unreacted excess alcohol.

13. A process as defined in claim 12 wherein the thin film is contacted with a sparging effective amount of an inert gas.

14. A process as defined in claim 13 wherein the inert gas is nitrogen.

15. A process as defined in claim 14 wherein the amount of inert gas is introduced in a countercurrent flow to the liquid film at about 0.56 weight % based on the feed rate to the evaporator.

16. A process as defined in claim 12 wherein the thin film is contacted with an inert gas in a non-sparging amount.

17. A process as defined in claim 16 wherein said inert gas is nitrogen.

18. A process as defined in claim 17 in which said inert gas is introduced into the evaporator in an amount of about 0.14 weight % based on the feed rate to the evaporator.

* * * * *